US005583281A

United States Patent [19]

Yu

[11] Patent Number: 5,583,281
[45] Date of Patent: Dec. 10, 1996

[54] MICROMINIATURE GAS CHROMATOGRAPH

[75] Inventor: Conrad M. Yu, Antioch, Calif.

[73] Assignee: The Regents of the University of California, Oakland, Calif.

[21] Appl. No.: 499,625

[22] Filed: Jul. 7, 1995

[51] Int. Cl.$^6$ ..................................................... G01N 30/20
[52] U.S. Cl. ........................................................... 73/23.42
[58] Field of Search ........................... 73/23.35, 23.37,
73/23.39, 23.4, 23.41, 23.42, 864.83; 55/270,
420; 96/105, 106, 101, 104, 107; 137/855,
856; 222/206; 417/566, 559, 560

[56] References Cited

U.S. PATENT DOCUMENTS

| | | | |
|---|---|---|---|
| 4,471,647 | 9/1984 | Jerman et al. | 73/23.4 |
| 4,895,500 | 1/1990 | Hok et al. | 137/855 X |
| 4,935,040 | 6/1990 | Goedert | 73/23.22 |
| 5,277,556 | 1/1994 | Van Lintel | 137/855 X |
| 5,313,061 | 5/1994 | Drew | 250/281 |
| 5,487,313 | 1/1996 | Johnson | 73/23.42 X |

*Primary Examiner*—Michael Brock
*Attorney, Agent, or Firm*—Henry P. Sartorio; Richard B. Main

[57] ABSTRACT

A microminiature gas chromatograph (μGC) comprising a least one silicon wafer, a gas injector, a column, and a detector. The gas injector has a normally closed valve for introducing a mobile phase including a sample gas in a carrier gas. The valve is fully disposed in the silicon wafer(s). The column is a microcapillary in silicon crystal with a stationary phase and is mechanically connected to receive the mobile phase from the gas injector for the molecular separation of compounds in the sample gas. The detector is mechanically connected to the column for the analysis of the separated compounds of sample gas with electronic means, e.g., ion cell, field emitter and PIN diode.

9 Claims, 4 Drawing Sheets

MICROMINIATURE GAS CHROMATOGRAPH

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to gas chromatography and more particularly to micro-instrumentation and the fabrication of sample gas injector valves in silicon wafers.

2. Description of Related Art

"Chromatography" is from the Greek word for "color writing." It is a method used in analytical chemistry to separate and identify the components of mixtures. The Russian botanist Mikhail S. Tswett (1872–1919) was the first (1903) to employ a general chromatographic technique. Partition chromatography was introduced in 1941, paper chromatography in 1944, and gas chromatography in 1952. A method of thin-layer chromatography was developed for general use in 1958. Since then, many chromatographic techniques have been developed that provide for specific needs, e.g., high performance, or pressure, liquid chromatography, gel permeation chromatography, ion chromatography, and concurrent chromatography. Prior art methods have emphasized both sensitivity and speed.

Column chromatography uses a vertical tube, or column, filled with a finely divided solid or liquid, a "stationary phase." A mixture of materials to be separated is placed at the top of the tube and is slowly washed down with a suitable liquid, eluent or carrying gas, a "mobile phase." As the mixture dissolves, each molecule is transported in the flowing liquid or carrying gas and becomes adsorbed into the stationary solid or liquid. Each type of molecule spends a different amount of time in the column, depending on its tendency to be adsorbed. Thus each compound descends through the column at a different rate. The various compounds stratify over physical distance in the column, as in a parfait.

Mobile phases may be gases or liquids, and stationary phases are either liquids adsorbed on solid carriers or solids. When a liquid stationary phase is used, the process is called partition chromatography, since the mixture to be analyzed will be partitioned, or distributed, between the stationary liquid and a separate liquid mobile phase. Where the stationary phase is solid, the process is known as adsorption chromatography. The molecules of the mixture to be separated pass many times between the mobile and stationary phases at a rate that depends on the mobility of the molecules, the temperature, and the binding forces involved. The difference in the time that each type of molecule spends in the mobile phase leads to a difference in the transport velocity and to the separation of substances.

Commonly used adsorbents are silica gel and alumina, which are powdered into particles between 0.05 and 0.2 mm (0.002 to 0.08 in) in diameter for optimal flow. Stationary phases with very different properties can be obtained; and many different mixtures can be separated if a suitable adsorbent is chosen, and the powder is impregnated with a liquid. Stepwise, or fractional, elution involves eluting with liquids of increasing or decreasing polarities. The emerging liquid eluate can be collected automatically in small portions by a fraction collector. Each fraction is then analyzed separately. The eluate may then be passed through a spectrophotometer that measures the light absorption when a specific substance leaves a column. For the analysis of substances still in the column, the solid can be carefully pushed out of the column, cut into small sections, and treated.

In thin-layer chromatography (TLC), the stationary phase is a thin layer on a glass plate or plastic film. Typical thin layers comprise one of the usual adsorbents, such as silica gel or alumina made into a slurry and dried in a homogeneous layer on the glass plate. The mixture to be separated is first dissolved in a volatile solvent, and a small sample of this solution is placed on the thin layer. The solvent is then evaporated, and only the mixture to be separated remains in the form of a small spot. The plate is placed in an upright position in a jar. A carefully chosen developing solvent is then added to the bottom, the atmosphere in the jar is completely saturated with the vapor of the eluent, and the dish is closed. The liquid rises along the plate by capillarity. When it has risen 10–15 cm (4–6 in), in 10–20 minutes, the development is stopped and the plate is dried. Most chromatograms can be examined under ultraviolet light to locate the compounds. However, if the compounds are colorless, the plate is sprayed with a special reagent that colors the various compounds. Paper chromatography uses a stationary phase of water adsorbed on paper and a mobile phase of an organic liquid and is similar to thin-layer chromatography.

Gas chromatography includes gas-liquid chromatography (GLC) and the far less common gas-solid (GSC) method. The stationary phase is a liquid on a solid support, which is pressed into a narrow, coiled column 1.5–5 m (4–15 ft) in length. The mobile phase is an inert gas, usually nitrogen, hydrogen, helium, or argon, which is passed through a heated column. The sample mixture is injected into the column and immediately vaporizes. Its constituent substances separate and flow at different rates with the carrier gas. A detector is placed at the end of the column, which outputs a signal to a recorder in the form of a gas chromatogram having a series of detector maximums. Each peak is characteristic of a particular substance in the sample gas.

An important part of each gas chromatograph is its detector. Various types have been developed, including the katharometer, the flame ionization detector, and the electron capture detector. The flame ionization detector can detect a sample as small as $10^{-11}$ grams of material. The electron capture detector is as much as 100 times more sensitive than that. As such, gas chromatography has become an essential analytical tool in many chemical laboratories.

High performance liquid chromatography, or high pressure liquid chromatography (HPLC), is a refinement of standard column chromatography and has become, along with GLC, one of the two most commonly used separative techniques. In HPLC, the particles that carry the stationary liquid phase are uniformly very small, e.g., 0.01 mm/0.0004 in. Thus, the stationary phase presents a large surface area to the molecules of the sample in the mobile liquid phase. A resistance to input pressure by a column filled with such small particles is overcome with a high-pressure pump to drive the mobile liquid phase through the column in a reasonable time. HPLC offers high resolution and sensitivity. A column of 25-cm (9.8-in) length has an overall efficiency of 10,000 plates or individual separations. HPLC can resolve a raw urine sample into 200 individual components. Its extraordinary sensitivity can be used to detect a concentration of one part in one billion of the chemical aflotoxin, which is toxic to humans in food concentrations of as little as ten parts in one billion. More recent HPLC's use smaller diameter columns (3–5 cm/1.2–2 in) that increase the analytic speed and conserve expensive solvents. Some units can now perform analyses in one minute or less.

Gel permeation chromatography is based on the filtering or sieving action of the stationary phase. The stationary phase material is selected from a set of adsorbents that have pores of uniform size in the range of 20 to 200 nm. While moving down the column loaded with this type of adsorbent, a molecule dissolved in the mobile liquid phase will be excluded from the adsorbent if its size is greater than that of the pores. If the molecular size is smaller, the molecule will become entrapped. Intermediate-size molecules will permeate some pores and not others. The result is a separation based on molecular size, with the larger molecules separating out first and the smaller molecules last. This technique is used to separate and measure the molecular weight of polymers, proteins, and other biological substances of high molecular weight.

Making gas chromatographs smaller has been an objective in the prior art. Drew, et al., describe in U.S. Pat. No. 5,313,061, issued May 17, 1994, a miniaturized mass spectrometer system. A battery-operated portable unit is used in the field to analyze the atmosphere, water, soil, drugs, explosives, and other substances. Such patent is incorporated herein by reference. Even though such a mass spectrometer system has been miniaturized, it is still quite large and not easily carried, e.g., as in a shirt pocket.

SUMMARY OF THE INVENTION

An object of the present invention is to provide a microminiature gas chromatograph.

A further object of the present invention is to provide a microminiature injector valve system in a silicon wafer for use in a gas chromatograph.

Briefly, an injector valve of the present invention comprises a flexible reed of silicon nitride attached to two silicon wafers that are bonded together to form a carrier gas channel with a normally closed side entry for a sample gas to pass the flexible reed. A sample gas pressure that is higher than the carrier gas pressure opens the valve and allows a mobile phase to flow and the separation of sample compounds in a column to proceed. A normally open valve is provided for the carrier gas supply with samples and also to regulate the pressure pumping of gas through the injector valve. It also allows the cleaning of the sample cavity.

A further advantage of the present invention is that a microminiature normally open valve is provided that can be constructed with silicon wafer fabrication techniques. An advantage of the present invention is that an injector is provided for a microminiature gas chromatograph.

An advantage of the present invention is that a high temperature injector of 350° C. or higher is provided for high resolution result.

Another advantage of the present invention is that inexpensive semiconductor fabrication techniques can be employed to make a microminiature gas valve and sample injector.

DETAILED DESCRIPTION OF THE INVENTION

Figure 1:
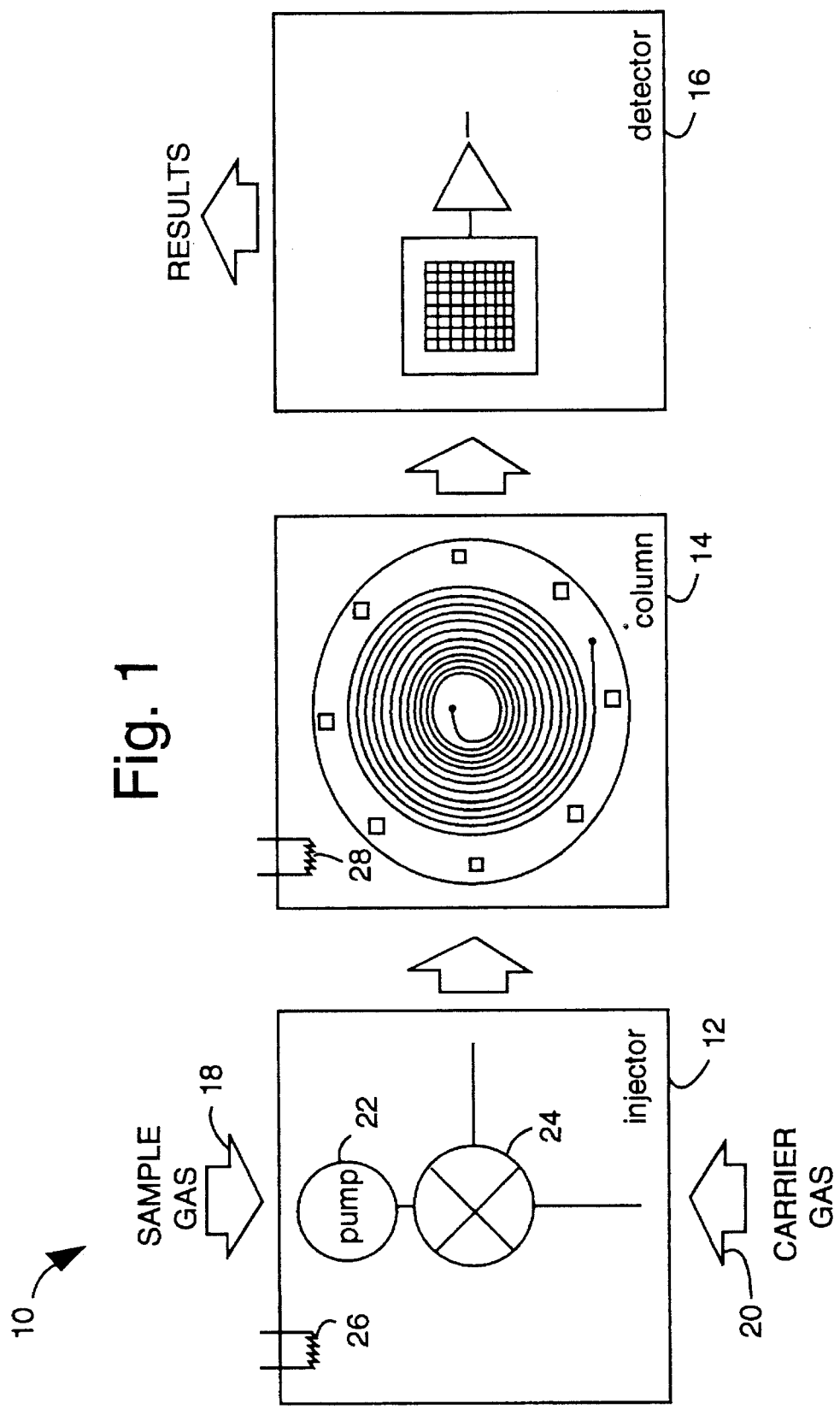
FIG. 1 is a block diagram of a microminiature gas chromatograph embodiment of the present invention.

FIG. 1 illustrates a microminiature gas chromatograph (μGC) in an embodiment of the present invention, referred to herein by the general reference numeral 10. The μGC 10 comprises an injector 12, a column 14 and a detector 16, each and all disposed in and fabricated from respective silicon wafers that have been bonded together in an assembly. Such silicon wafers are typically two inches in diameter. The column may be constructed according to the information provided in United States patent applications 08/464,020 and 08/465,068, filed Jun. 5, 1995, which are titled, METHOD FOR ETCHING MICROCHANNELS IN SILICON WAFERS TO HAVE SEMICIRCULAR CROSS SECTIONS and MICROCAPILLARY AND METHOD FOR JOINING SILICON WAFERS IN THE FABRICATION OF MICROCAPILLARIES, by the present inventor. Such applications are incorporated herein by reference.

The injector 12 receives a sample gas 18 and a carrier gas 20 for a mobile phase. A pump 22 allows a precision amount of the sample gas 18 to be injected into a valve 24 that then flows to the column 14. An electrical-resistance heater 26 is thermostatically controlled to maintain a constant temperature for the injector 12. Similarly, a heater 28 is thermostatically controlled to maintain a constant temperature for the column 14.

Figure 2A:
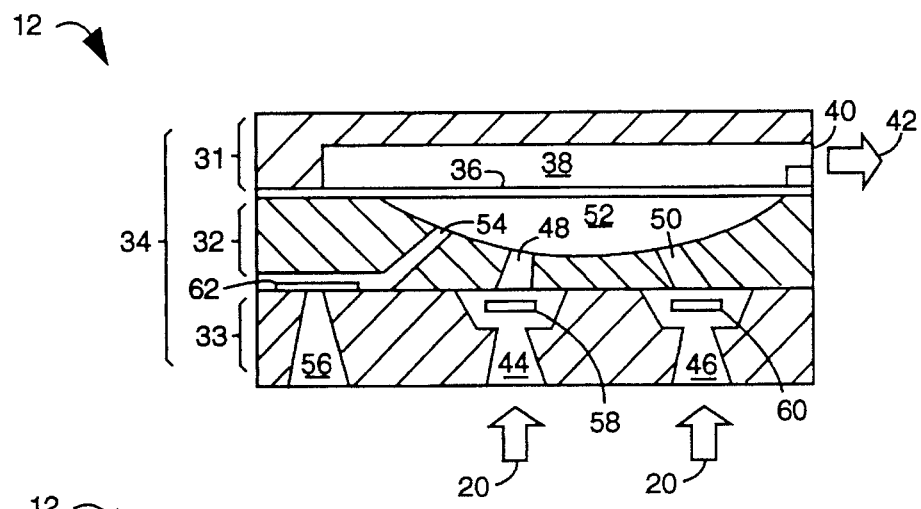
FIGS. 2A–2C are cross-sectional views of the injector in the microminiature gas chromatograph of FIG. 1.
Figure 2B:
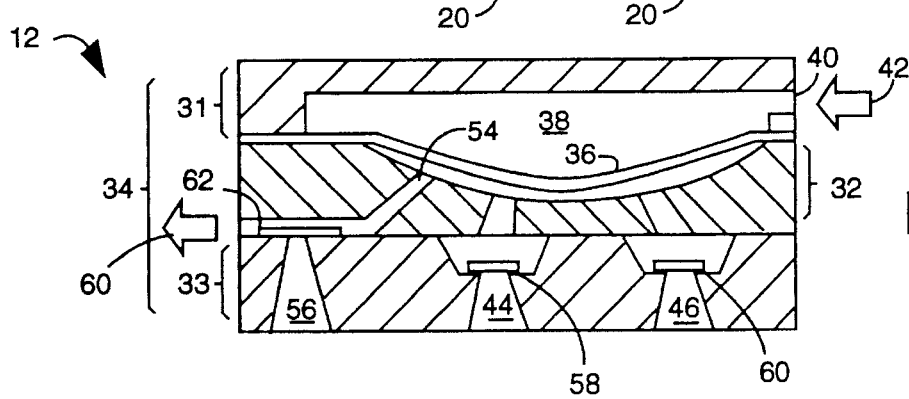
Figure 2C:
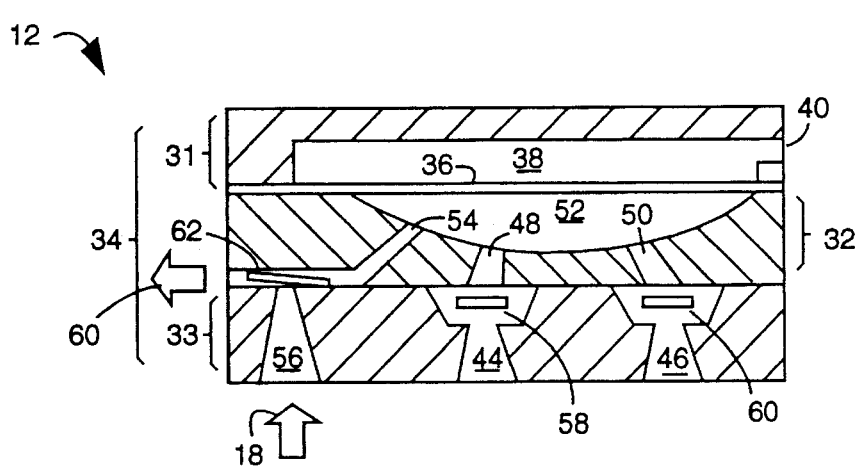

FIGS. 2A–2C represent the injector 12 in various operational states. A set of three silicon wafers 31–33 are bonded together in a stack 34. At the interface of wafers 31 and 32 is a silicon nitride membrane that contains a power driver volume 38. A port 40 is connected to a pneumatic system that provides pulses of air pressure punctuated by exhaust puffs 42. A pair of normally open valves 44 and 46 are connected by a pair of channels 48 and 50 to a precise sample volume cavity 52. The carrier gas 20 enters from the bottom through the normally open valves 44 and 46. An outlet 54 runs past a normally closed valve 56. The sample gas 18 enters the normally closed valve 56 from the bottom and is injected by superior pressure into the outlet 54 and flows out to the left.

In FIG. 2A, a pair of silicon nitride reeds 58 and 60 remain open, and a silicon nitride reed 62 remains closed. The carrier gas 20 is drawn into the cavity 52 through the channels 48 and 50.

In FIG. 2B, a pressure pulse forces the membrane 36 to bulge down into the cavity 52. The pair of silicon nitride reeds 58 and 60 are pressed down and closed. The silicon nitride reed 62 remains closed. The carrier gas 20 in the cavity 52 is forced out the outlet 54 into a mobile phase 60 that enters the column 14.

In FIG. 2C, the sample gas 18 is injected into the normally closed valve 56 under pressure sufficient to overcome the pressure of the carrier gas 20. The reed 62 opens and the sample gas 18 joins the mobile phase 60.

Figure 3:
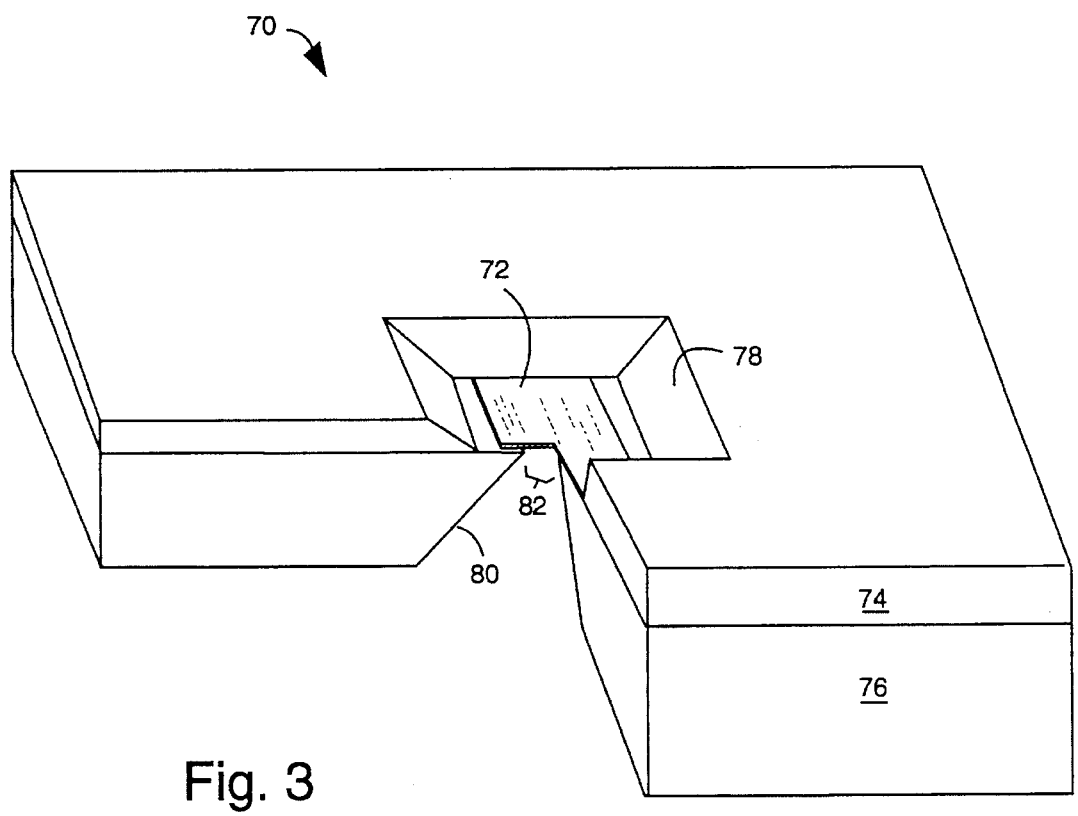
FIG. 3 is a perspective view of a normally-open valve similar to those in FIGS. 2A–2C.

FIG. 3 shows a normally open valve 70 that is similar to valves 44 and 46. A silicon nitride layer 72 is bonded between a pair of silicon wafers 74 and 76. The nitride layer 72 is suspended as a reed across an outlet opening 78 and allows gas to freely pass around it on two sides, because the opening 78 is substantially wider than the nitride layer 72.

An inlet opening 80 narrows to a small port 82 that is normally separated from the silicon nitride layer 72. But when a reverse pressure develops and gas tries to flow from the outlet 78 to the inlet 80, the silicon nitride layer deforms slightly and bulges down to seal against the port 82 and thus checks the reverse flow.

Figure 4A:
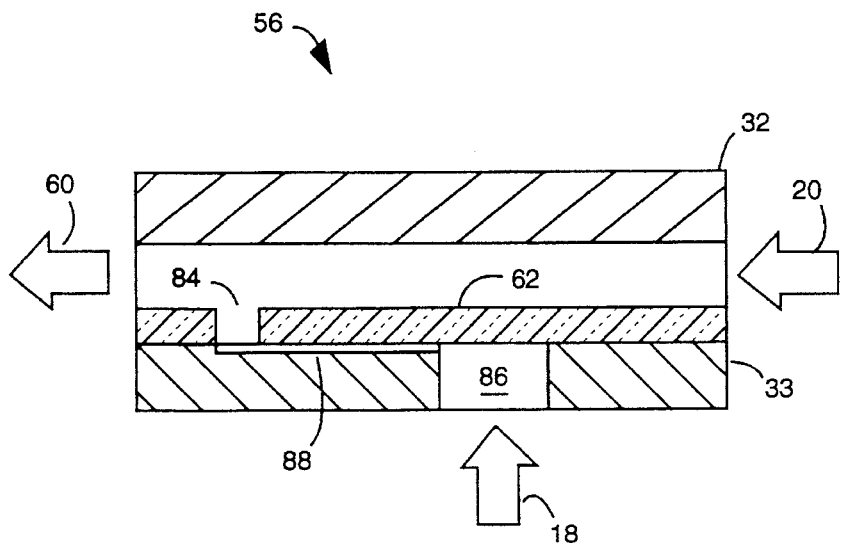
FIGS. 4A and 4B are cross-sectional diagrams of the normally-closed valve used in the injector of FIGS. 2A–2C.
Figure 4B:
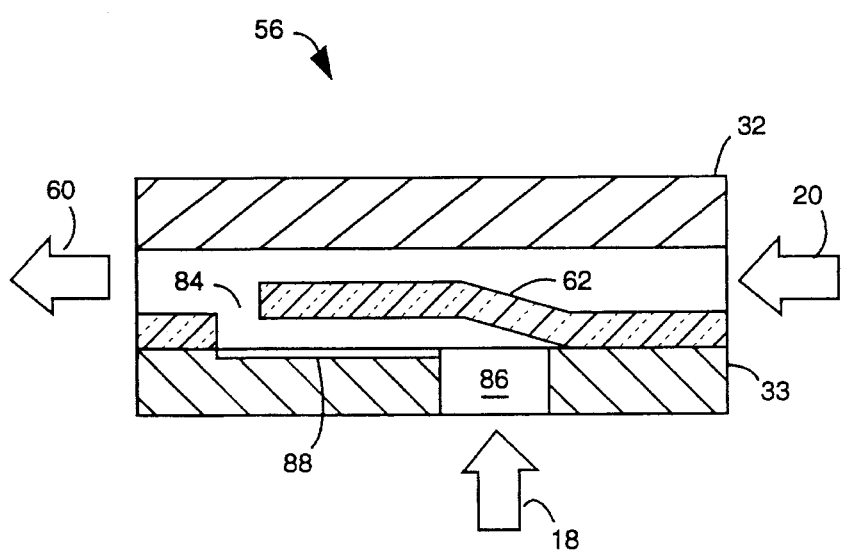

FIGS. 4A and 4B show the normally closed valve 56 in more detail. The silicon nitride reed 62 is a layer that is deposited on the wafer 33 and undercut by anisotropic etching between an exhaust port (or slit) 84 and a sample inlet port 86 to form a groove 88. The partially detached silicon nitride can then lip-open and serve as a reed valve. Preferably, the silicon nitride is attached on three of four edges such that only the fourth edge is free to open with a carrier gas 20, the silicon nitride reed 62 lifts up, as in FIG. 4B, to allow the slit. When the pressure of the sample gas 18 exceeds the pressure of the sample gas 18 to pass into the mobile phase 60.

In one alternative embodiment, the inlet port is one millimeter square, the exhaust port 84 is 200 microns by 50 microns, the layer 62 is 2000 angstroms thick, and the channel 54 is 500 microns wide and deep. The carrier gas 20 is under about 40 psi of pressure. The channel 88 is anisotropically etched with an HF buffer solution of ammonium fluoride ($NH_4F$) and hydrofluoric acid to partially detach the silicon nitride layer 62. The silicon wafers 31–33 are anhydrously bonded together.

Although particular embodiments of the present invention have been described and illustrated, such is not intended to limit the invention. Modifications and changes will no doubt become apparent to those skilled in the art, and it is intended that the invention only be limited by the scope of the appended claims.

The invention claimed is:

1. A microminiature gas chromatograph (μGC), comprising:

at least one silicon wafer;

a gas injector for introducing a mobile phase including a sample gas in a carrier gas and disposed in the silicon wafer(s);

a valve disposed in the gas injector and comprised of a layer of silicon nitride deposited on the silicon wafer and undercut by anisotropic etching between an exhaust port and a sample inlet port to form a groove, wherein a partially detached portion of said silicon nitride layer may lip-open to function as a normally closed valve, and wherein silicon nitride layer is attached on three of four edges of a valve perimeter such that only a fourth edge is free to open with a slit when the pressure of said sample gas exceeds the pressure of said carrier gas to allow said sample gas to pass into said mobile phase;

a column with a stationary phase and mechanically connected to receive said mobile phase from the gas injector for the molecular separation of compounds in said sample gas; and a detector mechanically connected to the column for the analysis of said separated compounds of sample gas with electronic means.

2. The μGC of claim 1, wherein:

the column comprises a microcapillary column disposed in a silicon wafer and mechanically connected to receive said sample gas in said carrier gas from the gas injector.

3. The μGC of claim 1, wherein:

the detector is disposed in a silicon wafer and mechanically connected to receive a separation of compounds of said sample gas in said carrier gas from the column.

4. The μGC of claim 1, wherein:

the gas injector further includes at least one normally open valve disposed in a silicon wafer.

5. The μGC of claim 4, wherein:

said normally open valve(s) comprise(s) a partially detached flap of silicon nitride providing for reed-valve opening and closing for introduction of said carrier gas to said mobile phase.

6. The μGC of claim 5, wherein:

the gas injector further includes a pump comprising a silicon nitride membrane that is flexibly distorted between a power driver volume and a precision cavity connected to said normally open valve(s) and said normally closed valve and providing for a pumping of said carrier gas into said column.

7. A microminiature gas chromatograph (μGC), comprising:

at least one silicon wafer;

a gas injector with a normally closed valve for introducing a mobile phase including a sample gas in a carrier gas, wherein said valve is fully disposed in the silicon wafer(s);

a column with a stationary phase and mechanically connected to receive said mobile phase from the gas injector for the molecular separation of compounds in said sample gas; and a detector mechanically connected to the column for the analysis of said separated compounds of sample gas with electronic means;

wherein, said normally closed valve comprises a partially detached film of silicon nitride providing for reed-valve opening and closing for introduction of said sample gas to said mobile phase.

8. A microminiature gas chromatograph (μGC), comprising:

at least one silicon wafer;

a gas injector with a normally closed valve for introducing a mobile phase including a sample gas in a carrier gas, wherein said valve is fully disposed in the silicon wafer(s);

a column with a stationary phase and mechanically connected to receive said mobile phase from the gas injector for the molecular separation of compounds in said sample gas; and a detector mechanically connected to the column for the analysis of said separated compounds of sample gas with electronic means;

wherein, the gas injector further includes at least one normally open valve fully disposed in the silicon wafer(s); and wherein, said normally open valve(s) comprise(s) a partially detached flap of silicon nitride providing for reed-valve opening and closing for introduction of said carrier gas to said mobile phase.

9. The μGC of claim 8, wherein:

the gas injector further includes a pump comprising a silicon nitride membrane that is flexibly distorted between a power driver volume and a precision cavity connected to said normally open valve(s) and said normally closed valve and providing for a pumping of said carrier gas into said column.

* * * * *